United States Patent [19]

Hoelderich et al.

[11] Patent Number: 4,904,806
[45] Date of Patent: Feb. 27, 1990

[54] PREPARATION OF TETRAHYDROFURANS FROM BUTANE-1,4-DIOLS

[75] Inventors: Wolfgang Hoelderich, Frankenthal; Matthias Schwarzmann, Limburgerhof, both of Fed. Rep. of Germany

[73] Assignee: BASF Aktiengesellschaft, Ludwigshafen, Fed. Rep. of Germany

[21] Appl. No.: 251,391

[22] Filed: Sep. 30, 1988

[30] Foreign Application Priority Data

Sep. 30, 1987 [DE] Fed. Rep. of Germany ....... 3732950

[51] Int. Cl.$^4$ ............................................ C07D 307/08
[52] U.S. Cl. ..................................................... 549/509
[58] Field of Search ......................................... 549/509

[56] References Cited

FOREIGN PATENT DOCUMENTS 0232712 8/1987 European Pat. Off. .
2461922 7/1976 Fed. Rep. of Germany .

OTHER PUBLICATIONS

Chemical Abstracts, Kh.I. Areshidze, vol.84, No.13, p.511, n.89.981a (1976).
Houben–Weyl, Vol. Sauerstoffverbindungen I Part 3, Georg Thieme Verlag, 1965) (English translation not readily available).
A. Molnar et al., Proc. ZEOCAT Symp. Siofok, Hungary, 1985, Acta Physica et Chemica Szegediensis, Sszeged. 1095, p. 571.
"Acta Physica et Chemica", pp. 571-578 (1985).

*Primary Examiner*—Richard L. Raymond
*Attorney, Agent, or Firm*—Keil & Weinkauf

[57] ABSTRACT

Tetrahydrofurans are prepared in the gas phase from butane-1,4-diols which may be substituted by alkyl, alkenyl and/or aryl radicals in the carbon skeleton. The reaction is carried out in the presence of a borosilicate and/or iron silicate zeolite, preferably of the pentasil type, as catalyst.

Other catalysts which may be used are zeolites doped with alkali metals and/or alkaline earth metals and/or transition metals and/or rare earth metals and/or noble metals.

2 Claims, No Drawings

PREPARATION OF TETRAHYDROFURANS FROM BUTANE-1,4-DIOLS

The present invention relates to a process for the preparation of tetrahydrofurans from butane-1,4-diols in the gas phase.

It is known that tetrahydrofuran can be prepared from butane-1,4-diol in the liquid phase in the presence of an acidic homogeneous catalyst, such as $H_2SO_4$, $H_3PO_4$ or toluenesulfonic acid, in high yields of about 95%. The disadvantage of this method is in the removal of the catalyst.

Sulfo-containing cation exchanger resins can also be used for this intramolecular dehydration. This procedure gives a yield of 92-95% (Houben-Weyl, Vol. Sauerstoffverbindungen I Part 3, Georg Thieme Verlag, 1965).

The reaction of diols over aluminosilicate zeolites of the X and Y type is likewise known (A. Molnar et al., Proc. ZEOCAT Symp. Siofok, Hungary, 1985, Acta Physica et Chemica Szegediensis, Sszeged, 1985, page 571). In addition to the desired dehydration, selectivity-reducing fragmentation of the carbon skeleton also occurs in this reaction.

It is an object of the present invention to synthesize tetrahydrofurans from butane-1,4-diols in very high yields over catalysts which have long lives.

We have found that this object is achieved and that tetrahydrofurans are obtained from butane-1,4-diols which may be substituted by alkyl, alkenyl and/or aryl radicals in the carbon skeleton, in the gas phase, in good yields and with long catalyst lives, if the reaction is carried out in the presence of a borosilicate and/or iron silicate zeolite as catalyst.

Butane-1,4-diols which have one or more linear, branched or cyclic alkyl and/or alkenyl radicals of 1 to 6 carbon atoms in the 1, 2, 3 and/or 4 position, and butane-1,4-diols which possess aryl and/or alkylaryl and/or aralkyl radicals of 6 to 12 carbon atoms exclusively or in addition to the alkyl and alkenyl radicals, and butane-1,4-diol can be used as starting materials.

The catalysts used for the novel process are borosilicate and iron silicate zeolites, borosilicate and iron silicate zeolites of the pentasil type being particularly suitable. These have a five-membered ring composed of $SiO_4$ tetrahedra, as a common basic building block.

The borosilicate zeolites are synthesized, for example, at from 90° to 200° C. under autogenous pressure by reacting a boron compound, eg. $H_3BO_3$, with a silicon compound, preferably finely divided silica, in aqueous amine solution, in particular in 1,6-hexanediamine or 1,3-propanediamine or triethylenetriamine solution, with or, in particular, without the addition of an alkali or alkaline earth. The isotactic zeolites according to German Laid-Open Application DOS 3,006,471 are also suitable. The borosilicate zeolites can also be prepared in solution in ether, eg. diethylene glycol dimethyl ether, or in alcoholic solution, eg. hexane-1,6-diol, instead of in aqueous amine solution.

The iron silicate zeolites are obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth, at from 100° to 220° C. under autogenous pressure.

The borosilicate and iron silicate zeolites thus prepared can be isolated, dried at from 100° to 160° C., preferably 110° C., and calcined at from 450° to 550° C., preferably 500° C., and then molded with a binder in a weight ratio of from 90:10 to 40:60 to give extrudates or pellets. Suitable binders are various aluminas, preferably boehmite, amorphous aluminum silicates having an $SiO_2/Al_2O_3$ ratio of from 25:75 to 95:5, preferably 75:25, silica, preferably finely divided $SiO_2$, mixtures of finely divided $SiO_2$ and finely divided $Al_2O_3$, and clay. After the molding procedure, the extrudates or pellets are dried at 110° C./16 hours and calcined at 500° C./16 hours.

Advantageous catalysts are also obtained if the borosilicate or iron silicate zeolites isolated are molded directly after drying and are not subjected to calcination until after the molding procedure. The borosilicate and iron silicate zeolites can be used in pure form, without a binder, as extrudates or pellets, examples of extrusion or peptizing assistants used being ethylcellulose, stearic acid, potato starch, formic acid, oxalic acid, acetic acid, nitric acid, ammonia, amines, silicoesters and graphite or mixtures of these.

If, because of the method of preparation, the zeolites are not in the acidic H form but, for example, in the Na form, the latter can be completely or partially converted into the desired H form by ion exchange, for example with ammonium ions, and subsequent calcination or by treatment with acids.

If, when the zeolite catalysts are used according to the invention, deactivation occurs as a result of coking, it is advisable to regenerate the zeolites by burning off the coke deposit with air or with an air/$N_2$ mixture at from 400° to 550° C., preferably 500° C. As a result, the zeolites regain their initial activity.

By precoking, it is possible to adjust the activity of the catalyst to obtain optimum selectivity with respect to the desired reaction products.

In order to obtain very high selectivity, high conversion and long catalyst lives, the zeolites may also be modified, for example by doping the unmolded or molded zeolites with metal salts by ion exchange or by impregnation. Suitable metals are alkali metals, such as Li or Cs, alkaline earth metals, such as Mg or Ca, transition metals, such as Cu, Fe, Zn or Co, noble metals, such as Pd or Pt, and rare earth metals, such as Ce or La.

The doping is advantageously carried out as follows: the molded zeolites are initially taken in a riser tube and an aqueous or ammoniacal solution of a halide or of a nitrate of the metals described above is passed over the said zeolite at from 20° to 100° C. Ion exchange of this type can be carried out on the hydrogen, ammonium and alkali metal form of the zeolite. In another possible method of applying metals to the zeolites, the zeolite material is impregnated with a halide, a nitrate or an oxide of the metals described above in aqueous, alcoholic or ammoniacal solution. Both ion exchange and impregnation may be followed by one or more drying steps and, if desired, by repeated calcination.

In a possible embodiment, for example, $Cu(NO_3)_2.3H_2O$ or $Ni(NO_3)_2.6H_2O$ or $Ce(NO_3)_3.6H_2O$ or $La(NO_3)_3.6H_2O$ or tungstic acid or $Cs_2CO_3$ is dissolved in water. This solution is used to impregnate the molded or unmolded zeolites for a certain time, for example about 30 minutes. The supernatant solution can be freed from water in a rotary evaporator. Thereafter, the impregnated zeolite is dried at about 150° C. and calcined at about 550° C. This impregnation process can be carried out several times in succession in order to obtain the desired metal content.

It is also possible to prepare an aqueous Ni(NO$_3$)$_2$ solution or ammoniacal Pd(NO$_3$)$_2$ solution or ammonium vanadate and to suspend the pure zeolite powder therein at from 40° to 100° C. for about 24 hours, while stirring. After filtration, drying at about 150° C. and calcination at about 500° C., the zeolite material thus obtained can be further processed with or without binders to give extrudates, pellets or fluidizable material.

The zeolites present in the H form, ammonium form or alkali metal form can be subjected to ion exchange by initially taking the zeolites in the form of extrudates or pellets in a column and circulating, for example, an aqueous Ni(CO$_3$)$_2$ solution or ammoniacal Pd(NO$_3$)$_2$ solution over the said zeolite at slightly elevated temperatures of from 30° to 80° C. for from 15 to 20 hours. The product is then washed with water, dried at about 150° C. and calcined at about 550° C. In the case of some metal-doped zeolites, for example Pd-, Cu- or Ni-doped zeolites, an aftertreatment with water is advantageous.

In another possible method of modification, the molded or unmolded zeolite material is subjected to a treatment with acids, such as hydrochloric acid, hydrofluoric acid and phosphoric acid, and/or steam. In this procedure, zeolites in powder form are advantageously treated with 1N phosphoric acid for 1 hour at 80° C. After the treatment, the product is washed with water, dried at 110° C. for 16 hours and calcined at 500° C. for 20 hours. In another procedure, zeolites, before or after they have been molded with binders, are treated with a 3-25, in particular 10-20, % strength by weight aqueous hydrochloric acid, for example for from 1 to 3 hours at from 60° to 80° C. The zeolite treated in this manner is then washed with water, dried, and calcined at from 400° to 500° C.

In a particular embodiment of the acid treatment, the zeolite material, before it has been molded, is treated at elevated temperatures with hydrofluoric acid, which is generally used in the form of 0.001-2N, preferably 0.05-0.5N, hydrofluoric acid, for example by refluxing for from 0.5 to 5, preferably from 1 to 3, hours. After it has been isolated, for example by filtering it off and washing it thoroughly, the zeolite material is advantageously dried at from 100° to 160° C. and calcined at from 450° to 600° C. In another preferred embodiment of the acid treatment, the zeolite material is molded with a binder at elevated temperatures and then treated at from 50° to 90° C., in particular from 60° to 80° C., for from 0.5 to 5 hours, in particular with from 12 to 20% strength by weight hydrochloric acid. The zeolite material is then washed thoroughly and is advantageously dried at from 100° to 160° C. and calcined at from 450° to 600° C.

In another procedure, zeolites can be modified by applying phosphorus compounds, such as trimethyl phosphate, trimethoxyphosphine or primary, secondary or tertiary sodium phosphate. Treatment with primary sodium phosphate has proven advantageous. In this procedure, the zeolites in the form of extrudates, pellets or fluidizable material, are impregnated with aqueous NaH$_2$PO$_4$ solution, dried at 110° C. and calcined at 500° C.

The catalysts described here can alternatively be used in the form of 2-4 mm extrudates, pellets having a diameter of from 3 to 5 mm or chips having particle sizes of from 0.1 to 0.5 mm or as a fluidized catalyst.

The reaction is preferably carried out in the gas phase at from 100° to 500° C., in particular from 150° to 300° C., and using a WHSV of from 0.1 to 20, in particular from 0.5 to 5, h$^{-1}$ (g of starting mixture per g of catalyst per hour). The reaction can be carried out in a fixed bed or a bed moving up and down or a fluidized bed.

It is also possible to carry out the reaction in the liquid phase (suspension, trickle-bed or liquid phase procedure) at from 50° to 200° C.

The process can be carried out under atmospheric, reduced or superatmospheric pressure and is preferably carried out by a continuous procedure.

Sparingly volatile or solid starting materials are reacted in dissolved form, for example in solution in tetrahydrofuran, toluene or petroleum ether. In general, the starting material can be diluted with such solvents or with inert gases, such as N$_2$, Ar or steam.

After the reaction, the resulting products are isolated from the reaction mixture by a conventional method, for example by distillation; unconverted starting mixture is, if desired, recycled to the reaction.

EXAMPLES 1-6

The reactions are carried out in the gas phase under isothermal conditions in a tube reactor (coil, 0.6 cm internal diameter, 90 cm length) in the course of not less than 6 hours. The reaction products are isolated and characterized by conventional methods. Quantitative determination of the reaction products and of the starting materials is carried out by gas chromatography.

The catalysts used for the novel process are:

Catalyst A

The borosilicate zeolite of the pentasil type is prepared in a hydrothermal synthesis from 640 g of finely divided SiO$_2$, 122 g of H$_3$BO$_3$ and 8,000 g of an aqueous 1,6-hexanediamine solution (weight ratio 50:50) at 170° C. under autogenous pressure in a stirred autoclave. The crystalline reaction product is filtered off, washed thoroughly, dried at 100° C. for 24 hours and calcined at 500° C. for 24 hours. This borosilicate zeolite is composed of 94.2% by weight of SiO$_2$ and 2.3% by weight of B$_2$O$_3$.

This material is molded with a molding assistant to give 2 mm extrudates, which are dried at 110° C. for 16 hours and calcined at 500° C. for 24 hours.

Catalyst B

The iron silicate zeolite of the pentasil type is synthesized under hydrothermal conditions, under autogenous pressure and at 165° C., from 273 g of waterglass, dissolved in 253 g of an aqueous 1,6-hexanediamine solution (weight ratio 50:50), and 31 g of iron sulfate, dissolved in 21 g of 96% strength sulfuric acid and 425 g of water, in a stirred autoclave in the course of 4 days. The zeolite is filtered off, washed thoroughly, dried at 110° C. for 24 hours and calcined at 500° C. for 24 hours. An iron silicate zeolite having an SiO$_2$/Fe$_2$O$_3$ ratio of 17.7 and an Na$_2$O content of 1.2% by weight is obtained. The catalyst is extruded to give 2.5 mm extrudates which are dried at 110° C. for 16 hours and calcined at 500° C. for 24 hours.

Catalyst C

The borosilicate zeolite (cf. catalyst A) is molded with boehmite in a weight ratio of 60:40 to give 2 mm extrudates, which are dried at 110° C. for 16 hours and calcined at 500° C. for 24 hours.

These extrudates are impregnated with aqueous $H_2WO_4$ solution, and the product is dried at 130° C. for 2 hours and calcined at 540° C. for 2 hours. The W content is 3.1% by weight.

Catalyst D

Catalyst A is impregnated with an aqueous $Ce(NO_3)_2$ solution, and the product is dried at 130° C. for 2 hours and calcined at 540° C. for 2 hours. The Ce content is 1.8% by weight.

The experimental results obtained with these catalysts and the reaction conditions are described in the Table below.

TABLE

| | Butane-1,4-diol →tetrahydrofuran + $H_2O$ | | | | | |
|---|---|---|---|---|---|---|
| Example | 1 | 1 | 3 | 4 | 5 | 6 |
| Catalyst | A | A | B | C | C | D |
| Temperature °C. | 200 | 300 | 200 | 200 | 300 | 200 |
| WHSV $h^{-1}$ | 1 | 2 | 1 | 2 | 2 | 1 |
| Conversion % | 100 | 100 | 100 | 100 | 100 | 100 |
| Selectivity % | 99.5 | 98.3 | 97.6 | 99.8 | 98.6 | 98.7 |

We claim:

1. A process for the preparation of a tetrahydrofuran from a butane-1,4-diol which may be substituted by alkyl, alkenyl and/or aryl radicals in the carbon skeleton, in the gas phase, wherein the reaction is carried out in the presence of a borosilicate and/or iron silicate zeolite of the pentasil type as the catalyst.

2. A process as defined in claim 1, wherein the catalyst used is doped with alkali metals and/or alkaline earth metals and/or transition metals and/or rare earth metals and/or noble metals.

* * * * *